United States Patent [19]

Montecalvo

[11] Patent Number: 5,727,550
[45] Date of Patent: Mar. 17, 1998

[54] DUAL PURPOSE ULTRASONIC BIOMEDICAL COUPLANT PAD AND ELECTRODE

[75] Inventor: David A. Montecalvo, Plymouth, Minn.

[73] Assignee: LecTec Corporation, Minnetonka, Minn.

[21] Appl. No.: 629,561

[22] Filed: Apr. 9, 1996

[51] Int. Cl.[6] .............................. A61B 5/04; A61B 8/00
[52] U.S. Cl. ................................ 128/640; 128/663.01
[58] Field of Search .............................. 128/639–641, 128/662.03, 663.01, 798, 802–803; 607/97, 149

[56] References Cited

U.S. PATENT DOCUMENTS

| | | | |
|---|---|---|---|
| 4,002,221 | 1/1977 | Buchalter | 181/0.5 |
| 4,089,329 | 5/1978 | Couvillon, Jr. et al. | 128/2 T |
| 4,125,110 | 11/1978 | Hymes | 128/2.06 E |
| 4,270,832 | 6/1981 | Tanabe | 339/105 |
| 4,274,420 | 6/1981 | Hymes | 128/641 |
| 4,299,231 | 11/1981 | Karmann et al. | 128/639 |
| 4,301,805 | 11/1981 | Peers-Trevarton | 128/419 |
| 4,349,030 | 9/1982 | Belgard et al. | 128/419 |
| 4,365,516 | 12/1982 | Molina | 73/644 |
| 4,458,696 | 7/1984 | Larimore | 128/798 |
| 4,459,854 | 7/1984 | Richardson et al. | 73/644 |
| 4,474,570 | 10/1984 | Ariura et al. | 604/20 |
| 4,515,162 | 5/1985 | Yamamoto et al. | 128/643 |
| 4,528,652 | 7/1985 | Horner et al. | 367/162 |
| 4,539,996 | 9/1985 | Engel | 128/640 |
| 4,556,066 | 12/1985 | Semrow | 128/639 |
| 4,577,643 | 3/1986 | Beranek | 128/785 |
| 4,674,512 | 6/1987 | Rolf | 128/640 |
| 4,675,009 | 6/1987 | Hymes et al. | 604/304 |
| 4,692,273 | 9/1987 | Lawrence | 128/640 |
| 4,694,835 | 9/1987 | Strand | 128/640 |
| 4,699,146 | 10/1987 | Sieverding | 128/640 |
| 4,702,732 | 10/1987 | Powers et al. | 604/20 |
| 4,706,680 | 11/1987 | Keusch et al. | 128/640 |
| 4,717,378 | 1/1988 | Perrault et al. | 604/20 |
| 4,785,822 | 11/1988 | Wallace | 128/675 |
| 4,825,876 | 5/1989 | Beard | 128/675 |
| 4,920,972 | 5/1990 | Frank et al. | 128/675 |
| 4,989,607 | 2/1991 | Keusch et al. | 607/152 |
| 5,002,792 | 3/1991 | Vegoe | 128/639 |
| 5,036,857 | 8/1991 | Semmlow et al. | 128/715 |

(List continued on next page.)

FOREIGN PATENT DOCUMENTS

| | | | |
|---|---|---|---|
| 2552611 | 9/1983 | France | H04R 1/46 |
| 61-120053 | 6/1986 | Japan | G01N 27/30 |
| 3254730 | 11/1991 | Japan | A61B 5/02 |
| 1546900A1 | 4/1986 | U.S.S.R. | G01N 29/00 |
| 2045088 | 10/1980 | United Kingdom | A61B 5/04 |
| WO81 00785 | 3/1981 | WIPO | H01B 1/06 |

OTHER PUBLICATIONS

"Peripheral Vascular Noninvasive Measurements" *Encyclopedia of Medical Devices and Instrumentation.* J. Webster (ed.); Wiley & Sons, New York, 1988; pp. 2220–2238.

*Introduction to Biomedical Equipment Technology.* Carr and Brown; John Wiley & Sons, New York. pp. 294–298.

*Primary Examiner*—Francis Jaworski
*Attorney, Agent, or Firm*—James V. Harmon

[57] ABSTRACT

A dual purpose biomedical device has a solid flexible ultrasonic couplant sheet or pad formed from an electrically conductive hydrogel. The hydrogel sheet has an upper surface that is exposed during use for allowing direct contact between an ultrasonic generator and the hydrogel sheet and a lower surface that is placed during use against the skin of a patient whereby the hydrogel sheet transmits ultrasonic waves to and from the body of the patient. An adhesive is operatively associated with the hydrogel sheet for adhering the sheet to the skin. A removable and replaceable electrically conductive flexible sheet is supported upon the upper surface of the hydrogel sheet for establishing electrical contact with the patient through the hydrogel sheet when lowered into contact with the hydrogel sheet. The conductive sheet is removable therefrom for allowing the ultrasonic generator to contact the hydrogel sheet.

10 Claims, 3 Drawing Sheets

U.S. PATENT DOCUMENTS

| | | | |
|---|---|---|---|
| 5,109,863 | 5/1992 | Semmlow et al. | 128/715 |
| 5,123,423 | 6/1992 | Schamberg | 607/152 |
| 5,125,405 | 6/1992 | Schmid | 128/639 |
| 5,205,297 | 4/1993 | Montecalvo et al. | 128/798 |
| 5,394,877 | 3/1995 | Orr et al. | 128/662.03 |
| 5,450,845 | 9/1995 | Axelgaard | 128/640 |
| 5,474,065 | 12/1995 | Meathrel et al. | 128/640 |
| 5,522,878 | 6/1996 | Montecalvo et al. | 607/152 |

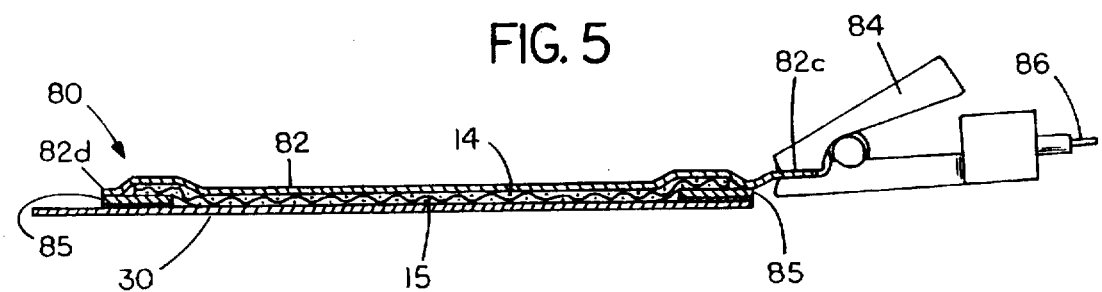
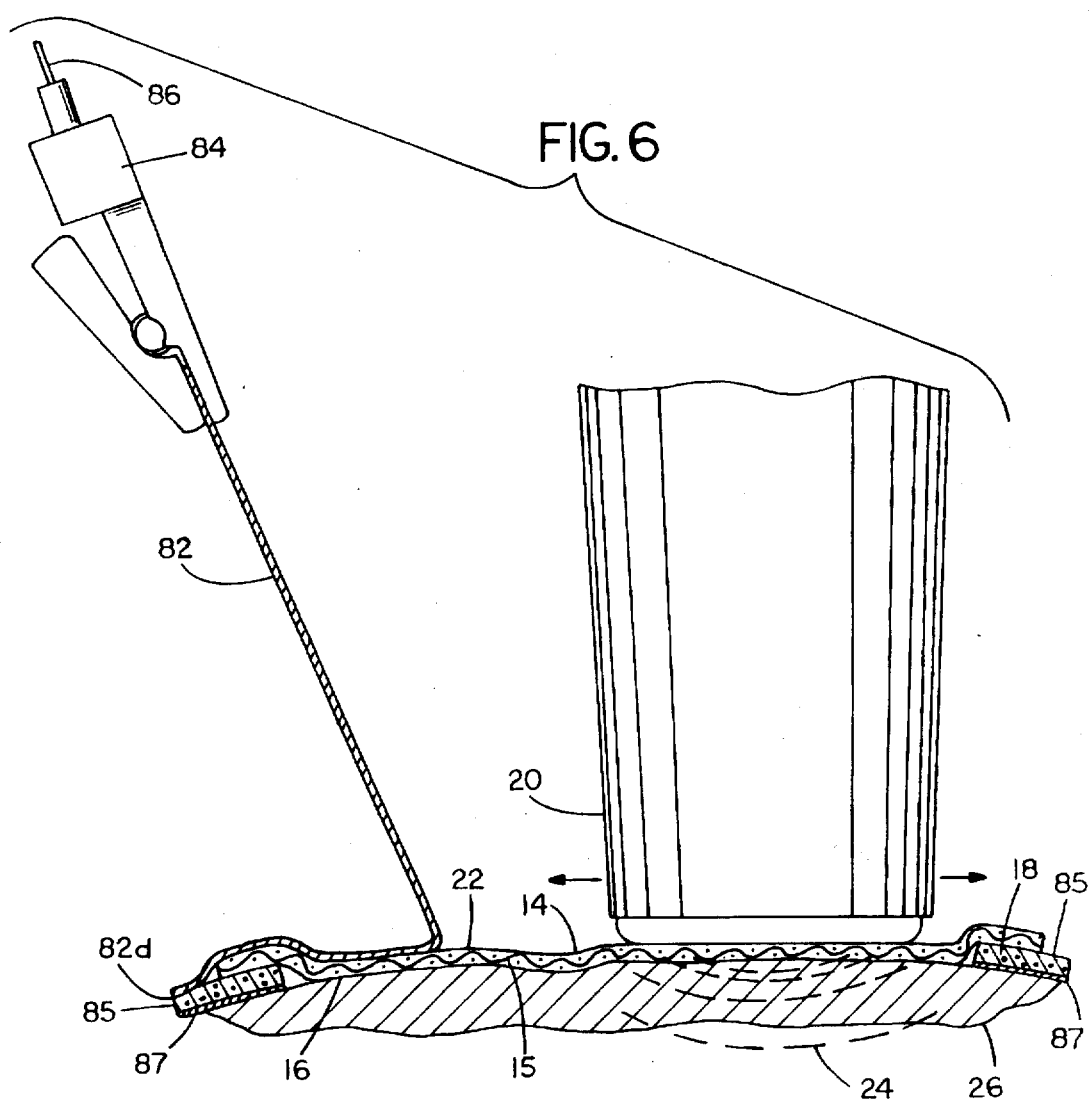

5,727,550

DUAL PURPOSE ULTRASONIC BIOMEDICAL COUPLANT PAD AND ELECTRODE

FIELD OF THE INVENTION

The present invention relates to biomedical devices and more particularly to an externally applied ultrasonic couplant pad that can also function as a biomedical electrode.

BACKGROUND OF THE INVENTION

Skin-contacting electrode sensors have been used successfully for some time in providing substantially interference-free transfer of cardiovascular (CV) signals to electrocardiographic equipment for making ECG measurements, producing displays or for providing electrical stimulation to the body of a patient. In this procedure, disposable external electrode sensors for ECG readings are placed in contact with a patient at selected locations about the torso or limbs. These sensors are held adhesively to the skin surface and include a conductive gel or membrane that chemically reduces the resistance presented by the skin and thereby promotes the transmission of CV electrical impulses from the body of the patient via the electrodes to the associate detecting means. In the hospital emergency room, intensive care or critical care facility, it is also sometimes desirable to assess peripheral blood flow by the Doppler ultrasound method for the purpose of assuring that there is adequate blood flow to the extremities. Performing these operations must be convenient and easily accomplished by the health care worker. Moreover, monitoring under emergency conditions can sometimes be a life and death matter, and therefore convenience and ease of use is extremely important.

It is a general objective of the invention to provide a convenient way to facilitate the monitoring of both CV signals and blood flow from a single point of attachment to the body. It is also an objective to provide a way of enabling the heart monitoring connection to remain coupled when pulse detection is made to save time both procedures and to minimize the effect of one procedure on the other. A more specific object is to provide a single unit or appliance that will facilitate both CV and blood flow monitoring. Another object is to reduce costs by eliminating the expense of providing two separate appliances. A further object is to provide the convenience of mounting a single appliance that takes the place of two separate appliances. Still another object is to provide a biomedical monitoring system that leaves the chest area unobstructed which is advantageous in facilitating examination of the patient and administering further therapeutic procedures.

Biomedical electrodes that are attached to the skin of a patient for transmitting electrical impulses to and from the body have not been successful in certain applications. For example, efforts have been made in the past to develop a less expensive, disposable monitoring electrode for receiving electrical signals from the body. These efforts failed in certain applications due to the high cost of the electrode where the electrode was only used once and then disposed of. Therefore, another object is to overcome this difficulty by providing a unique dual purpose product in which a single hydrogel sheet functions both in ultrasonic biomedical coupling for transmitting ultrasonic energy to and from the body as well as an electrical conductor in a biomedical electrode for transmitting electrical signals from the body or to the body of the patient.

These and other more detailed and specific objects of the present invention will be better understood by reference to the following brief summary which describes by way of example but a few of the various forms of the invention within the scope of the appended claims.

SUMMARY OF THE INVENTION

The present invention provides a dual purpose ultrasonic biomedical couplant pad or sheet that also serves as an electrode for transmitting electrical signals to or from the body. The couplant sheet has broad upper and lower spaced-apart top and bottom surfaces and an edge which is usually circular, square or rectangular but can have other shapes such as the shape of the part of the body being monitored. The sheet is flexible and holds its own shape, i.e., is a flexible solid. During use, the lower surface of the sheet is applied to the skin of a patient and remain in place throughout use. The ultrasound instrument is then placed in any position in contact with the exposed upper surface of the sheet and, if desired, can be passed back and forth, usually while in contact with the exposed upper surface of the gel sheet as ultrasound energy is transmitted through the gel sheet which serves as a transmission path for the sonic energy entering and leaving the body of the patient. The invention also includes an upper electrically conductive layer removably applied to the hydrogel sheet or pad which serves both as an electrical conductor for transmitting electrical signals to and from the electrically conductive layer through the skin of the patient as well as serving as an ultrasonic biomedical couplant layer for transferring sonic energy from an ultrasonic transducer into and out of the body of the patient. There is also a feature which allows the electrically conductive layer to be moved between a deployed position and an inactive position in which it remains attached to the hydrogel pad.

DESCRIPTION OF THE PREFERRED EMBODIMENTS

Any of various known ultrasonic scanning devices are employed with the present invention, such as those employed for medical diagnostic purposes which utilize sound transducers to transmit ultrasonic waves (e.g., on the order of several megahertz) into a patient and also detect echo signals. The echo signals are converted to electrical signals by the transducer, and the electrical signals are electronically processed and used to control display apparatus for depicting either the internal structure of a patient or for evaluating blood flow as in the case of a Doppler ultrasound transducer in which the sonic energy reflected from the blood contained in the ankle or hand provide a way of assessing the volume of blood passing through the extremity beneath the transducer.

In use, the invention acts as a dual purpose sensor that is suited for both ultrasonic sensing and electrical sensing. The invention is preferably used as an ultrasonic couplant sheet for transferring ultrasonic energy in detecting blood flow using a Doppler ultrasound instrument as well as a monitoring electrode for sensing electrical signals received from the body, particularly cardiovascular (CV) electrical signals showing the activity of the heart muscle. While useful primarily for the purpose of transmitting CV signals from the body to a recording instrument, it can be used if desired for transferring signals in the opposite direction, i.e., from a device to the body. The invention is especially useful in recording electrocardiogram signals during surgical operations, in the emergency room, or in the intensive care unit (ICU) or to mitigate pain through the transmission of electrical pulses to the body or as a grounding pad.

The base of the sensor is a hydrophilic hydrogel sheet which is made electrically conductive and remains bonded to the skin throughout use for the purpose of insuring good electrical contact between the electrode and the skin of the patient. The removable and replaceable electrically conductive layer secured to the top of the hydrogel sheet enables the device to serve as a highly functional monitoring electrode. While some previous attempts to market disposable single-use electrodes have been unsuccessful commercially, the present invention provides a cost advantage because the hydrogel monitoring layer used in the present invention for ultrasound measurements has a dual purpose. Moreover, the presence of the electrically conductive sheet makes the invention useful for monitoring electrical signals from the body without having to apply additional electrodes to the skin.

The hydrogel sheet of the present invention is a flexible, self-supporting solid sheet which holds its form during storage and when placed on the body, not an amorphous fluid gel of the type commonly used for fetal monitoring. The hydrogel sheet has a slippery upper surface. The lubricity of the hydrogel sheet facilitates sliding movement of the ultrasound instrument from one portion of the sheet to another as readings are taken. The hydrogel sheet consists of two major components: a liquid and a network of long polymer molecules that hold the liquid in place to give the gel a degree of solidity. Fluid gels previously used were dispensed from a collapsible tube. In these gels there is only enough friction between the polymer molecules to hinder rapid flow, causing the fluid to be thick and viscous. At higher concentrations, the polymer coils intertwine so as to give the gel visco-elastic properties but will still allow a gel to flow enough so that it can be smeared over the skin with the fingers or with a spatula and leaves a residue that requires cleanup following use. By contrast, in the present invention the gel is not a fluid but is a flexible solid that is sufficiently "set" so that the dispersion of the polymer strands will not flow when manipulated. Therefore, the gel of the present invention has a particular shape and retains that shape even after being placed on the body. Moreover, if perturbed mechanically, it will eventually separate along a fracture line or it can be torn when pulled apart by hand. It is flexible, somewhat elastic, conforms easily to the body contours, and is preferably somewhat tacky, at least on the lower surface so as to establish a mechanical connection or bond with the skin to enhance the transfer of ultrasound energy but leaves no residue and requires no cleanup.

The hydrogel sheet includes a solid phase comprising a natural or synthetic hydrophilic polymer which is dispersed in a liquid phase to provide the flexible but solid hydrogel matrix. The liquid phase of the matrix preferably includes water together with a hydrophilic humectant such as a polyhydric alcohol, i.e., one having two or more hydroxyl groups. Optionally, in one preferred form of the invention, a minor amount of a gelation inhibitor is included in an amount sufficient to reduce the viscosity of the matrix as it is being formed into a sheet to prevent premature gelation, i.e., setting of the matrix structure prior to conversion into sheet form as, for example, by the application of the hydrogel as it is being formed onto a backing or supporting sheet.

In one preferred forming process the hydrogel is made by coating it while still formable onto a flexible backing sheet, i.e., a liner sheet, usually paper or plastic film. Removable sheets cover both the upper and lower surfaces of the hydrogel sheet. The coveting sheets, which enclose the hydrogel sheet and also keep it clean during shipment and storage, are usually weakly adhesively bonded to the upper and lower surface of the hydrogel by the tacky surface character of the hydrogel sheet so that they can be removed prior to use. The lower surface of the hydrogel sheet is exposed before use to contact the body of a patient directly during use and preferably forms a removable adhesive bond with the skin.

The hydrogel sheet of the present invention functions as an interface or transducer between the ultrasound device and the skin as the device emits the ultrasound waves. During use, the hydrogel sheet transmits the bursts of ultrasound energy produced in the device to the target and also transmits a portion of the energy reflected back to the receiver contained in the ultrasound device. The hydrogel sheet of the present invention can be used, for example, in procedures for monitoring fetal activity and movement (as in transabdominal Doppler ultrasound). However, the invention is especially useful in plethysmography in which the volume of an organ or part of the mammalian body is ascertained through a change in the quantity of blood therein. The invention is especially advantageous in evaluating peripheral vascular disease through Doppler echocardiography in which blood flow is assessed through peripheral vascular non-invasive ultrasound measurements.

During use, a patch of the hydrogel sheet is applied to a patient and can be used repeatedly, i.e., the hydrogel sheet is reusable and will remain attached to the skin between periods of use. The hydrogel sheet can also be covered which enables it to resist moisture gain or loss either prior to or during use.

The ultrasonic couplant sheets of the present invention are substantially uniform in thickness and remain so throughout use as they efficiently transfer sonic energy, and optionally, electrical energy, to and from the body of the patient. They are easy to apply and use; they are supple, pliable, soft will conform to the skin contours. If desired, either the upper or lower surface, or both, can be easily moistened with water or otherwise lubricated just prior to or during use. They are non-irritating, have no odor and are safe to use. They also preferably cling to the skin and thus remain in place on the skin during use, but afterwards can be easily removed and require little, if any, cleanup.

The electrically conductive flexible sheet is removably and replaceably supported upon the upper surface of the hydrogel sheet for establishing electrical contact with the skin of a patient through the hydrogel layer when lowered into contact with the hydrogel sheet, but when removed it exposes the broad upper surface of the hydrogel sheet so that the ultrasonic generator can be placed in contact with the hydrogel sheet for transferring sonic wave energy to and from the patient. The flexible electrically conductive sheet can be removed by being lifted manually or replaced at any time desired. The electrically conductive sheet is preferably permanently connected to the hydrogel layer which acts as a support and a hinge is provided at one edge of the sheet for keeping the electrically conductive sheet in position for re-application to the upper surface of the hydrogel layer.

THE FIGURES

FIG. 5 is a side view of the sensor of FIGS. 1–4 partly in section;

FIG. 6 is a side view of the sensor of FIG. 5 as it appears when used for ultrasonic blood flow monitoring;

DETAILED DESCRIPTION OF THE INVENTION

Figure 1:
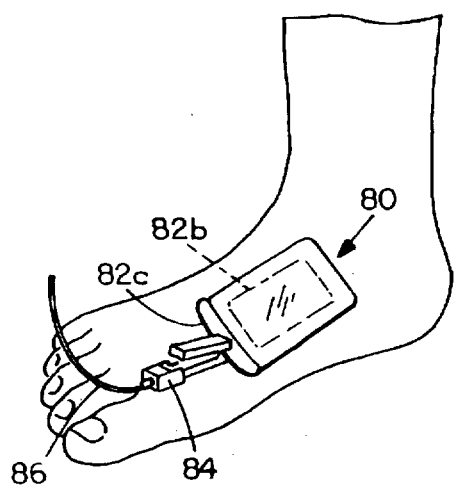
FIG. 1 is a perspective view of the invention applied to the foot of a patient for dual purpose monitoring of blood flow and electrical signals from the body.

Refer now to the figures and particularly to FIGS. 1–4 which illustrate a dual purpose couplant device 80 embodying the invention. The couplant device 80 includes a patch of flexible hydrogel material 14 having a composition as described in U.S. patent application Ser. No. 08/054,745, now U.S. Pat. No. 5,522,878.

The flexible hydrogel sheet 14 is a rectangular sheet of solid material has a lower surface 16 which is exposed just prior to use and is preferably tacky so that it will form a removable mechanical, i.e., adhesive bond to the surface of the skin 18 (FIG. 2) after being applied.

Figure 2:
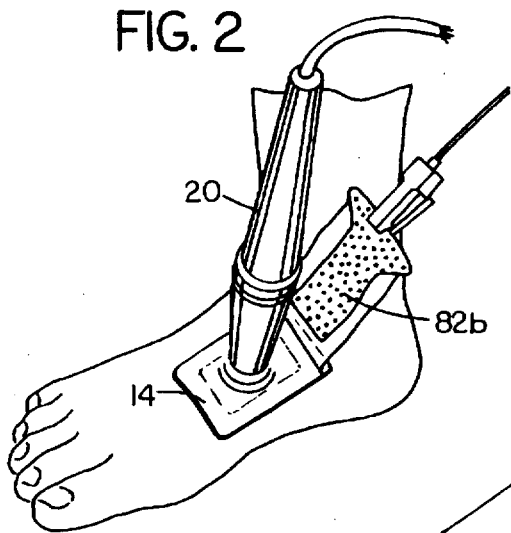
FIG. 2 is a perspective view of the dual purpose sensor of FIG. 1 while it is being used for blood flow monitoring.

It will be seen especially in FIG. 2 that the sheet of flexible hydrogel material 14 is substantially uniform in thickness throughout so that during use a standard ultrasound instrument 20 (FIG. 2) can be placed in contact with the upper surface 22 (FIG. 6) of the hydrogel sheet 14 and slid back and forth wherever desired by the healthcare professional, causing ultrasound waves 24 to be passed into the body 26 and then received by the ultrasound instrument 20 from the body of the patient.

The hydrogel sheet 14 is enclosed, i.e., surrounded with a frame or border 85, preferably formed from a sheet of plastic foam such as foamed polyurethane, polyethylene, or foamed rubber, etc. bonded to the edge of sheet 14. The border 85 has a layer of adhesive 87, preferably a pressure-sensitive adhesive, applied to its lower surface. The couplant device 80 also includes a second removable protective layer 30 applied to the lower surface 16 of hydrogel sheet 14 and to the adhesive layer 28 of the border 85.

Figure 4:
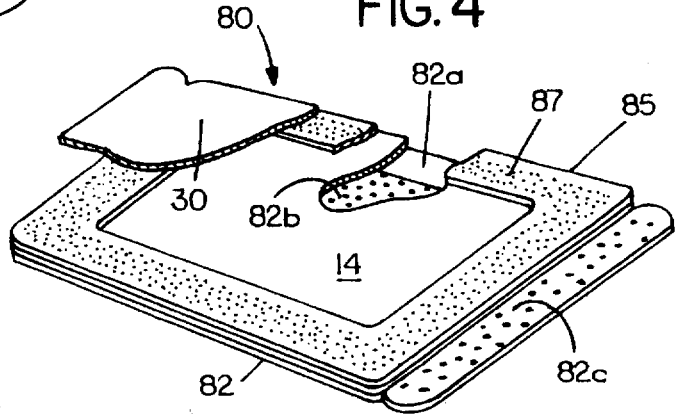
FIG. 4 is a bottom perspective view of the dual purpose sensor of FIGS. 1–3.

FIG. 4 shows the couplant device 80 prior to use with both of the removable protective layers 12 and 30 in place. To use the couplant device 80, the lower protective layer 30 is removed first. The couplant device 80 is then applied to the skin as shown in FIGS. 1 and 2. As this is done, the adhesive 87 will form a bond with the skin as will the tacky lower surface 16 of the hydrogel sheet 14 so that each serves as a means for adhering the hydrogel sheet to the skin of the patient.

The hydrogel layer 14 can be of any thickness but is preferably between about 10–100 mils and usually about 80 mils thick. The polyethylene foam ting 85 is typically about 0.064 inches in thickness. As shown in FIG. 6, the hydrogel sheet 14 is supple, flexible and conforms to the contours of the body 26 during use. It can be kept in place on the body over an extended period of time and used periodically, and can then be removed without the requirement for cleanup simply by lifting one edge and peeling it away from the skin. In hospitals where a reading is taken periodically, e.g., every hour or so, the invention is very advantageous since the hydrogel sheet 14 can be left in place on the skin of the patient throughout the entire period of time that the diagnostic information is taken, e.g., 24 hours.

The natural lubricity of the hydrogel sheet 14 facilitates movement of the instrument 20. Because the hydrogel sheet 14 is uniform in thickness, precise readings can be obtained throughout use. The normally tacky lower surface 16 of the hydrogel sheet 14 establishes good mechanical contact by providing a removable bond with the skin to help enhance the transmission of ultrasound waves 24 (FIG. 6) to and from the body.

Refer now to FIGS. 1 and 2 which illustrate the couplant device of the present invention for use in peripheral vascular non-invasive ultrasound measurements. In this application, pulsed Doppler instrumentation is used to detect blood flow; that is to say, for plethysmography. The flexible hydrogel sheet 14 is shown as it is appears when applied to the top of the foot. As this is done the bottom surface 16 of the hydrogel sheet 14, as well as the adhesive at 87 on the lower surface of the border or frame 85 forms an adhesive bond with the skin to thereby hold the hydrogel sheet 14 in place during use.

When a different blood vessel is used, the couplant device 80 including the hydrogel sheet 14 together with the plastic foam border 85 can be applied to the side of the foot in the ankle area or to any other area. The couplant device is held in place reliably by means of the pressure-sensitive layer 87 on the lower surface of the foam border 85 as well as by the tacky lower surface of the hydrogel sheet 14. Once applied, the ultrasound instrument, such as the Doppler ultrasound transducer 20, is placed in contact with the exposed upper surface 22 of the hydrogel sheet 14 to make readings. If desired, the instrument can be slid about on the upper surface 22 of the hydrogel sheet 14 until operation is optimized.

Typical formulations for the hydrogel couplant sheet are shown in the following examples.

|  | Optimum Weight Range As A % by Weight of the Hydrogel Sheet | Typical (%) |
| --- | --- | --- |
| Example 1 | | |
| Polyacrylamide | 10–40 | 10 |
| Triethylene Glycol | 10–50 | 15 |
| Glycerin | 10–50 | 12.5 |
| Water | 10–70 | 59 |
| Mg(OAc)$_2$ | 1–12 | 2.5 |
| NaCl | 1–20 | 1 |
| Example 2 | | |
| Polyacrylamide | 10–40 | 12 |
| Glycerin | 10–50 | 30 |
| Water | 10–70 | 54 |
| Mg(OAc)$_2$ | 1–12 | 3 |
| NaCl | 1–20 | 1 |
| Example 3 | | |
| Polyacrylamide | 10–40 | 15 |
| Triethylene Glycol | 10–50 | 20 |
| Glycerin | 10–50 | 15 |
| Water | 10–70 | 48 |
| NaCl | 1–20 | 2 |
| Example 4 | | |
| Polyacrylamide | 10–30 | 15 |
| Maltodextrin (a partially hydrolyzed starch)* | 5–15 | 10 |
| Glycerin | 20–60 | 49 |
| Water | 1–70 | 18 |
| Mg(OAc)$_2$ | 1–12 | 1 |
| NaCl | 1–20 | 7 |

*Lodex 10 ® by American Maize Products Company of Hammond, Indiana

As shown in FIGS. 5 and 6, the hydrogel layer 14 in the device 80 is provided with an internal cloth or scrim layer 15 and the edges of the hydrogel layer 14 are attached to the border 85 which serves to anchor the entire device with the required stability for long-term adhesion; for example, during the entire time that the patient is in the intensive care unit. The hydrogel sheet 14 of the device 80 is rendered electrically conductive by the addition of a suitable electrolyte, e.g., sodium chloride, in the amount of about 1% to 20% to provide an electrical conductivity, typically of about 1 to 1000 ohms/square and most preferably about 1 to 100 ohms/square.

Figure 3:
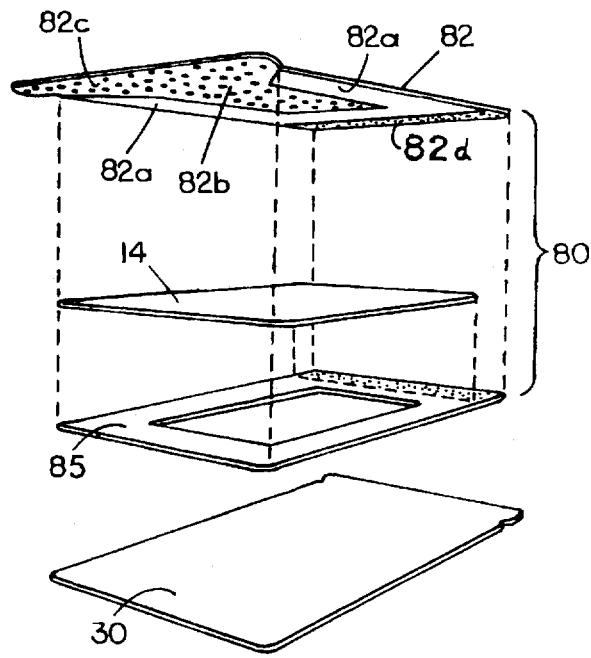
FIG. 3 is an exploded perspective view of the invention shown in FIGS. 1, 2 and 4.

The device 80 is suited for two electrical and ultrasonic sensing. This objective is achieved by providing a removable and replaceable electrically conductive sheet 82 on the top of the device 80. The electrically conductive sheet 82 preferably includes a backing 82a, e.g., a sheet of 0.05 mm polyester film to which is applied an electrically conductive coating 82b of any suitable type known in the art, e.g., free metal such as silver, gold, copper, nickel, zinc, aluminum or tin, or a printed coating such as an electrically conductive carbon or graphite based ink or a coating of silver covered with a coating of silver chloride. The electrically conductive coating 82b can be applied by printing or by vacuum electro-deposition from a vapor state. As best shown in FIGS. 2 and 3, the electrically conductive coating 82b is located at the center of the backing 82 with an uncoated border surrounding three sides and has an electrically conductive tab 82c at one end which is coupled during use to electrical instrumentation 88 by means of an electrically conductive alligator clip or clasp 84 having an electrical conductor or wire 86 which leads to the monitoring instrument 88.

The left end of the electrically conductive sheet 82 as seen in FIGS. 5 and 6 is connected by a permanent adhesive bond at 82d to the foam border ring 85. The adhesive bond 82d serves as a retainer or support for anchoring the electrically conductive sheet 82 in place on the sensor, and a portion of sheet 82 next to the bond 82d acts as a hinge which allows the sheet 82 to be raised and lowered as many times as desired.

Figure 7:
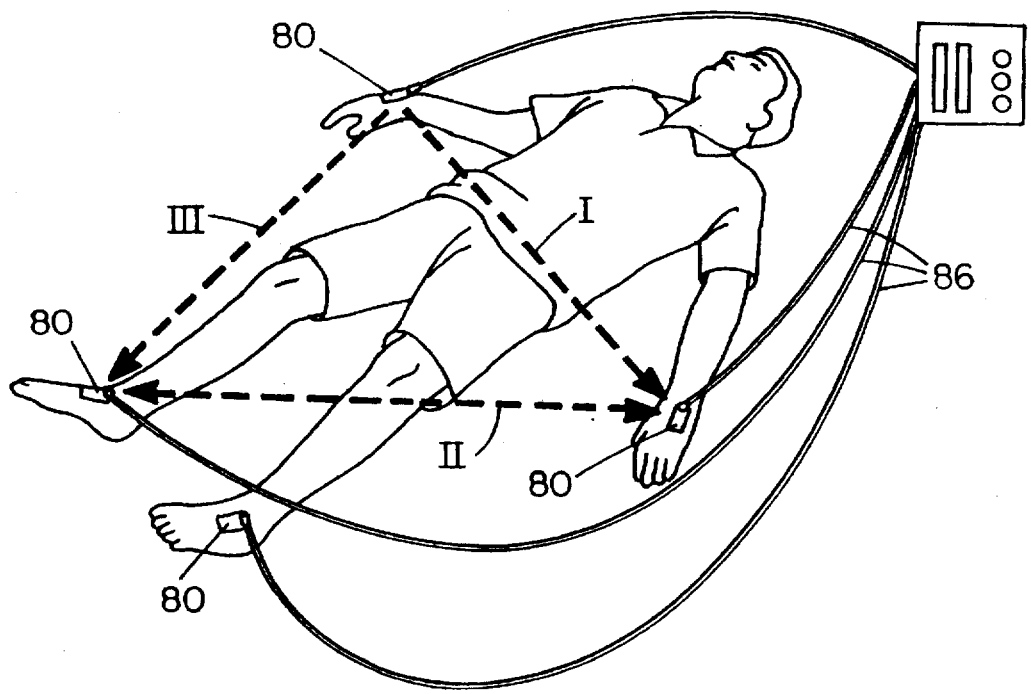
FIG. 7 is a perspective view showing four of the dual purpose sensors of the invention in use for electrocardiograph monitoring.

FIG. 7 shows four such electrical conductors or lead wires 86 connected to four of the devices 80 for monitoring heart activity. The four devices 80 are applied to the wrist and ankles. When the electrical monitoring is carried out, the electrically conductive sheet 82 is lowered into contact with the upper surface 22 of the hydrogel layer 14. However, when the ultrasound instrument 20 is to be used, the electrically conductive sheet 82 is lifted manually as shown in FIG. 6 so the ultrasound instrument 20 can be placed in contact with the hydrogel layer 14 and then moved by sliding it back and forth as required for optimal measurement.

After the ultrasound instrument 20 has been removed, the electrically conductive sheet 82 is again lowered manually to the position of FIG. 5 so that electrical monitoring can continue.

When the removable and replaceable electrically conductive sheet 82 is deployed as shown in FIG. 5, electrical contact is established with the upper surface 22 of the hydrogel layer 14 to the tab 82c. This enables the instrument 88 to be useful for monitoring heart activity. In monitoring heart activity as shown in FIG. 18, the vector designated I between the right and left arms represents a potential which when combined with a second vector II between the left arm and right leg to result in a third vector III representing a resultant ECG signal depicting the electrical activity of the patient's heart. The device 80 on the left leg, in this case, serves as a grounding pad.

As soon as heart monitoring is completed, the electrically conductive layer 82 is elevated as shown in FIG. 6, and the ultrasonic generator 20 is again placed in contact with the exposed surface 22 of the hydrogel layer 14 which then serves to conduct sonic energy to and from the body through the skin. The upper surface 22 of the hydrogel layer 14 provides natural lubricity to facilitate movement of the instrument 20 (which in this case is used as a Doppler ultra-sonic transducer) from one location to another on the upper surface of the sheet 14 to enable the operator to make ultrasonic measurements in different areas or from different directions until operation of the transducer 20 and its associated instrumentation is optimized for achieving the best possible blood flow measurement.

Figure 8:
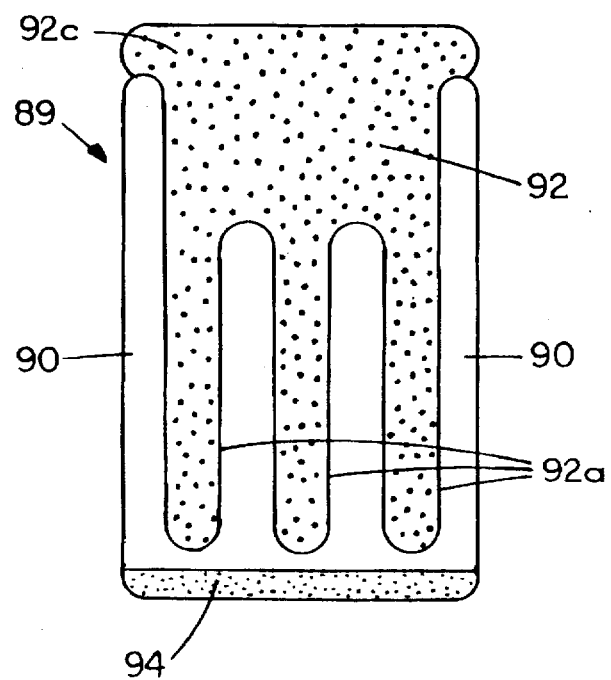
FIG. 8 is a bottom plan view of another form of electrically conductive sheet in accordance with the invention.

Refer now to FIG. 8 which shows another form of electrically conductive sheet 89 in accordance with the invention. As shown in the figure, electrically conductive sheet 89 has a backing sheet 90 for support, which can be plastic film to which is applied an electrically conductive coating or film 92 of any suitable known composition or as described above, e.g., a film of silver covered by a layer of silver chloride which does not cover the entire area of the backing sheet 90 but instead includes three parallel legs 92a separated by uncoated areas. This construction is particularly useful in lowering manufacturing costs if the coating 92 is formed completely or in part from a precious metal. The portion along one edge of the electrically conductive sheet 90 that is bonded by adhesive to the foam border 85 is designated 94.

Many variations of the present invention within the scope of the appended claims will be apparent to those skilled in the art once the principles described herein are understood.

What is claimed is:

1. A dual purpose biomedical device comprising,
    a solid flexible ultrasonic couplant sheet formed from an electrically conductive hydrogel having an upper surface that is exposed during use for allowing direct contact between an ultrasonic generator and the hydrogel sheet,
    the hydrogel sheet has a lower surface for being placed against the skin of a patient whereby the hydrogel sheet transmits ultrasonic waves to and from the body of the patient,
    means operatively associated with the hydrogel sheet for adhering the hydrogel sheet to the skin of the patient, and
    a removable and replaceable electrically conductive flexible sheet supported upon the upper surface of the hydrogel sheet for establishing electrical contact with the patient through the hydrogel sheet when lowered into contact with the hydrogel sheet and being removable therefrom for allowing the ultrasonic generator to contact the hydrogel sheet.

2. The biomedical device of claim 1 wherein a portion of the electrically conductive sheet is attached in fixed relationship to the hydrogel sheet and a remaining portion of the electrically conductive sheet can be raised and lowered manually to remove the electrically conductive sheet or replace the conductive sheet in contact with said upper surface of the hydrogel sheet.

3. The biomedical device of claim 1 wherein the electrically conductive sheet has an attached portion at one end that is bonded to said device and an electrically conductive tab portion on an opposite edge thereof from the attached portion for making contact with an electrical conductor for carrying current to and from the device.

4. The biomedical device of claim 1 wherein the electrically conductive sheet comprises a flexible backing sheet formed from a non-conductor of electricity and a layer of an electrically conductive material supported upon a surface thereof facing said upper surface of the hydrogel sheet for making electrical contact therewith when the electrically conductive sheet is lowered into contact with the hydrogel sheet.

5. The device of claim 4 wherein the electrically conductive layer comprises an applied layer of an electrical conductor selected from gold, silver, silver chloride, copper, nickel, aluminum, zinc, tin, carbon or graphite.

6. The biomedical device of claim 1 wherein the couplant sheet has a perimeter and means for adhering the hydrogel sheet is a border formed from a flexible sheet of material connected to the perimeter to encircle the hydrogel sheet, and the border has an adhesive coating thereon to bond the couplant sheet to the skin of a patient.

7. The biomedical device of claim 1 wherein the hydrogel couplant sheet is made electrically conductive by the presence of an electrolyte therein and the electrically conductive flexible sheet has an electrically conductive tab for establishing electrical contact with the skin of a patient through the hydrogel sheet when the electrically conductive sheet is lowered into contact with the hydrogel sheet.

8. The biomedical device of claim 1 wherein the flexible electrically conductive sheet is hinged to the hydrogel sheet.

9. The biomedical device of claim 1 wherein the flexible electrically conductive sheet is bonded along one edge thereof to the device and has an electrically conductive tab at an opposite end that can be lowered or raised when desired to expose the upper surface of the couplant sheet for the application of an ultrasonic transducer thereto and, following removal of the transducer from the hydrogel sheet, the electrically conductive sheet can be lowered again into contact with the exposed surface of the hydrogel sheet to reestablish electrical contact therewith for monitoring electrical signals from the body of the patient.

10. The device of claim 9 wherein the electrically conductive sheet is a sheet of plastic film having an electrically conductive layer on a lower surface thereof including one of the following: carbon, graphite, silver, copper, nickel, tin, gold, aluminum, zinc or silver chloride.

* * * * *